US 9,421,134 B2

(12) United States Patent
Schlinz et al.

(10) Patent No.: US 9,421,134 B2
(45) Date of Patent: Aug. 23, 2016

(54) METHOD OF MANUFACTURING ABSORBENT ARTICLES HAVING A WAISTBAND

(75) Inventors: Daniel R. Schlinz, Greenville, WI (US); WenTong Lay, Appleton, WI (US); Nancy E. Dawson, Appleton, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 500 days.

(21) Appl. No.: 13/071,638

(22) Filed: Mar. 25, 2011

(65) Prior Publication Data

US 2012/0241078 A1 Sep. 27, 2012

(51) Int. Cl.
| | |
|---|---|
| *B29C 65/00* | (2006.01) |
| *A61F 13/15* | (2006.01) |
| *A61F 13/539* | (2006.01) |
| *A61F 13/49* | (2006.01) |
| *B29C 65/48* | (2006.01) |
| *B32B 37/14* | (2006.01) |

(52) U.S. Cl.
CPC ..... *A61F 13/15601* (2013.01); *A61F 13/15804* (2013.01); *A61F 13/49011* (2013.01); *A61F 13/49017* (2013.01); *A61F 13/539* (2013.01); *B29C 65/00* (2013.01); *B29C 65/48* (2013.01); *B32B 37/144* (2013.01); *B32B 2307/51* (2013.01); *B32B 2555/02* (2013.01); *Y10T 156/1052* (2015.01); *Y10T 156/1066* (2015.01); *Y10T 156/1075* (2015.01)

(58) Field of Classification Search
CPC .............. A61F 13/49017; A61F 13/49011; A61F 13/539; B29C 65/00; B29C 65/48; Y10T 156/1052; Y10T 156/1066; Y10T 156/1075

USPC .................................... 604/386, 390
See application file for complete search history.

(56) References Cited

U.S. PATENT DOCUMENTS

| | | |
|---|---|---|
| 4,515,595 A | 5/1985 | Kievit et al. |
| 4,568,344 A | 2/1986 | Suzuki et al. |
| 4,585,447 A | 4/1986 | Karami |
| 4,943,340 A | 7/1990 | Ujimoto et al. |
| 5,236,430 A | 8/1993 | Bridges |
| 5,242,436 A | 9/1993 | Weil et al. |
| 5,358,500 A | 10/1994 | Lavon et al. |
| 5,527,304 A | 6/1996 | Buell et al. |
| 5,540,796 A * | 7/1996 | Fries .............................. 156/164 |
| 5,542,942 A | 8/1996 | Kline et al. |
| 5,545,158 A | 8/1996 | Jessup |
| 5,569,232 A | 10/1996 | Roe et al. |
| 5,593,401 A | 1/1997 | Sosalla et al. |

(Continued)

FOREIGN PATENT DOCUMENTS

| | | |
|---|---|---|
| WO | 9618367 | 6/1996 |
| WO | 9730671 | 8/1997 |

(Continued)

*Primary Examiner* — Mark A Osele
*Assistant Examiner* — Nickolas Harm
(74) *Attorney, Agent, or Firm* — Armstrong Teasdale LLP

(57) ABSTRACT

A method of manufacturing an absorbent article includes directing a web of side panel material and a waist elastic material separate from the web of side panel material to travel. The waist elastic material is bonded to the web of side panel material. The web of side panel material having the waist elastic material bonded thereto is cut to form a side panel having a waistband portion. The side panel having the waistband portion is attached to a chassis.

24 Claims, 8 Drawing Sheets

(56) References Cited

U.S. PATENT DOCUMENTS

| | | |
|---|---|---|
| 5,843,068 A | 12/1998 | Allen et al. |
| 6,022,471 A * | 2/2000 | Wachter et al. ........... 208/120.01 |
| 6,558,499 B1 * | 5/2003 | Pargass et al. ................. 156/250 |
| 6,702,795 B2 | 3/2004 | Klemp |
| 6,780,272 B2 * | 8/2004 | Wood ............................ 156/250 |
| 7,172,667 B2 * | 2/2007 | Vergona ......................... 156/64 |
| 7,718,021 B2 * | 5/2010 | Venturino et al. ............ 156/73.1 |
| 7,833,369 B2 * | 11/2010 | Zhou et al. .................... 156/73.1 |
| 7,918,961 B2 * | 4/2011 | Wada et al. .................... 156/259 |
| 8,323,443 B2 * | 12/2012 | Wada et al. .................... 156/259 |
| 8,529,536 B2 * | 9/2013 | Tsang et al. ................ 604/385.3 |
| 2002/0032427 A1 | 3/2002 | Schmitz et al. |
| 2002/0173767 A1 | 11/2002 | Popp et al. |
| 2004/0122411 A1 | 6/2004 | Hancock-Cooke |
| 2004/0243086 A1 | 12/2004 | VanGompel et al. |
| 2006/0069376 A1 | 3/2006 | Miller et al. |
| 2007/0005037 A1 * | 1/2007 | Mansfield et al. ......... 604/385.3 |
| 2008/0234649 A1 | 9/2008 | Hamall et al. |
| 2008/0311338 A1 | 12/2008 | Petersen et al. |
| 2009/0143756 A1 | 6/2009 | Hornung et al. |
| 2009/0157034 A1 | 6/2009 | Mattingly et al. |
| 2009/0240229 A1 | 9/2009 | Malowaniec |
| 2009/0312734 A1 | 12/2009 | LaVon et al. |

FOREIGN PATENT DOCUMENTS

| | | |
|---|---|---|
| WO | 9818421 | 5/1998 |
| WO | 9945880 | 9/1999 |

* cited by examiner

METHOD OF MANUFACTURING ABSORBENT ARTICLES HAVING A WAISTBAND

FIELD

The field of the invention relates generally to a method of manufacturing absorbent articles, and more particularly to a method of manufacturing absorbent articles having a waistband adapted to fully encircle a waist of a wearer.

BACKGROUND

Exemplary absorbent articles include training pants, diapers, incontinence products, disposable underwear, medical garments, absorbent swim wear, and the like. Training pants (albeit, not exclusively) are disposable absorbent articles for use in the toilet training process. Toilet training is a process that includes many training techniques and aids that can be used by parents or other caregivers. One aspect of the total toilet training process is changing from the use of diapers to the use of training pants to help the child understand that he or she should now use the toilet.

Many caregivers underestimate the difficulty of teaching the toilet training process to young children. If a child does not respond to an initial toilet training instruction or introduction, the caregiver can be at a loss for finding techniques, methods, or teaching tools to encourage the child to master the art of toilet training. Thus, while various teaching tools such as books, videotapes, charts with stickers, personalized toilets, and interactive toilet training kits are available, there remains a need for improved motivational mechanisms to facilitate the toilet training process.

One motivational mechanism is the use of training pants having an improved aesthetic appearance. Specifically, a child is encouraged to wear a garment that resembles underwear worn by older children. Thus, there is an ongoing need to increase the appeal of the toilet training process to children, and to improve the aesthetic appearance of training pants. However, it is important that any modifications to the training pants to meet these needs do not compromise the use of the articles or any functional features of the articles (e.g., wetness indicators).

Current training pants typically include a chassis, a pair of front side panels, and a pair of back side panels. The front and back side panels extending outward from the chassis and are joined together, either permanently or refastenablely, in respective pairs to form sides of the training pants. An elastic waistband material is often bonded to the chassis adjacent its longitudinal ends to form a gather waistband of the training pants. The side panels, however, are often free from the waistband material. That is, the waistband material is not typically located on the side panels.

Thus, the waistband material is discontinuous and extends around only a portion of a wearer's waist during use. Moreover, the gathers formed by the waistband, which are only in the chassis of training pants, are absent from the side panels making the lack of waistband material from the side panels more obvious. As a result, current training pants have a waistband that is significantly and obviously different from typical underwear, which have a fully encircling waistband. In addition, the discontinuous waistband of typical training pants detracts from their aesthetic appearance.

Moreover, the waist opening of conventional training pants is often defined in part by the chassis and in part by the side panels. As a result of the waistband material being located only on the chassis, typical training pants are substantially more stretchable in the chassis area that corresponds to the waistband as compared to the side panels. In other words, the portion of the chassis having the waistband material is much more stretchable than the side panels. This discrepancy in stretchability can result in the trainings pants being difficult for the user to pull up and down in the same manner in which underwear are pulled up and down.

Accordingly, a training pant having a fully encircling waistband and a manufacturing method that enables a waistband to be placed on the side panels of a training pant to form a fully encircling waistband is desirable.

BRIEF DESCRIPTION

In one aspect, a method of manufacturing an absorbent article generally comprises directing a web of side panel material to travel and directing waist elastic material separate from the web of side panel material to travel. The waist elastic material is bonded to the web of side panel material. The web of side panel material having the waist elastic material bonded thereto is cut to form a side panel having a waistband portion. The side panel having the waistband portion is attached to a chassis.

In another aspect, a method of manufacturing an absorbent article generally comprises bonding waist elastic material to a web of side panel material. The web of side panel material having the waist elastic material bonded thereto is cut to form at least two side panels. Waist elastic material is bonded to a chassis in at least one of a front waist region and a back waist region of the chassis. The at least two side panels are attached to the chassis such that the waist elastic material on the at least two side panels is generally aligned with the waist elastic material in at least one of a front waist region and a back waist region of the chassis.

In yet another aspect, a method of manufacturing an absorbent article generally comprises stretching a web of side panel material in a machine direction and stretching a waist elastic material in the machine direction. The waist elastic material is bonded to the web of side panel material while both the waist elastic material and the web of side panel material are stretched. The web of side panel material having the waist elastic material bonded thereto is cut to form at least two side panels. Waist elastic material is bonded to a chassis. The at least two side panels are attached to the chassis such that the waist elastic material on the at least two side panels is generally aligned with the waist elastic material on the chassis.

BRIEF DESCRIPTION OF THE DRAWINGS

Corresponding reference characters indicate corresponding parts throughout the drawings.

DETAILED DESCRIPTION OF THE DRAWINGS

Figure 1:
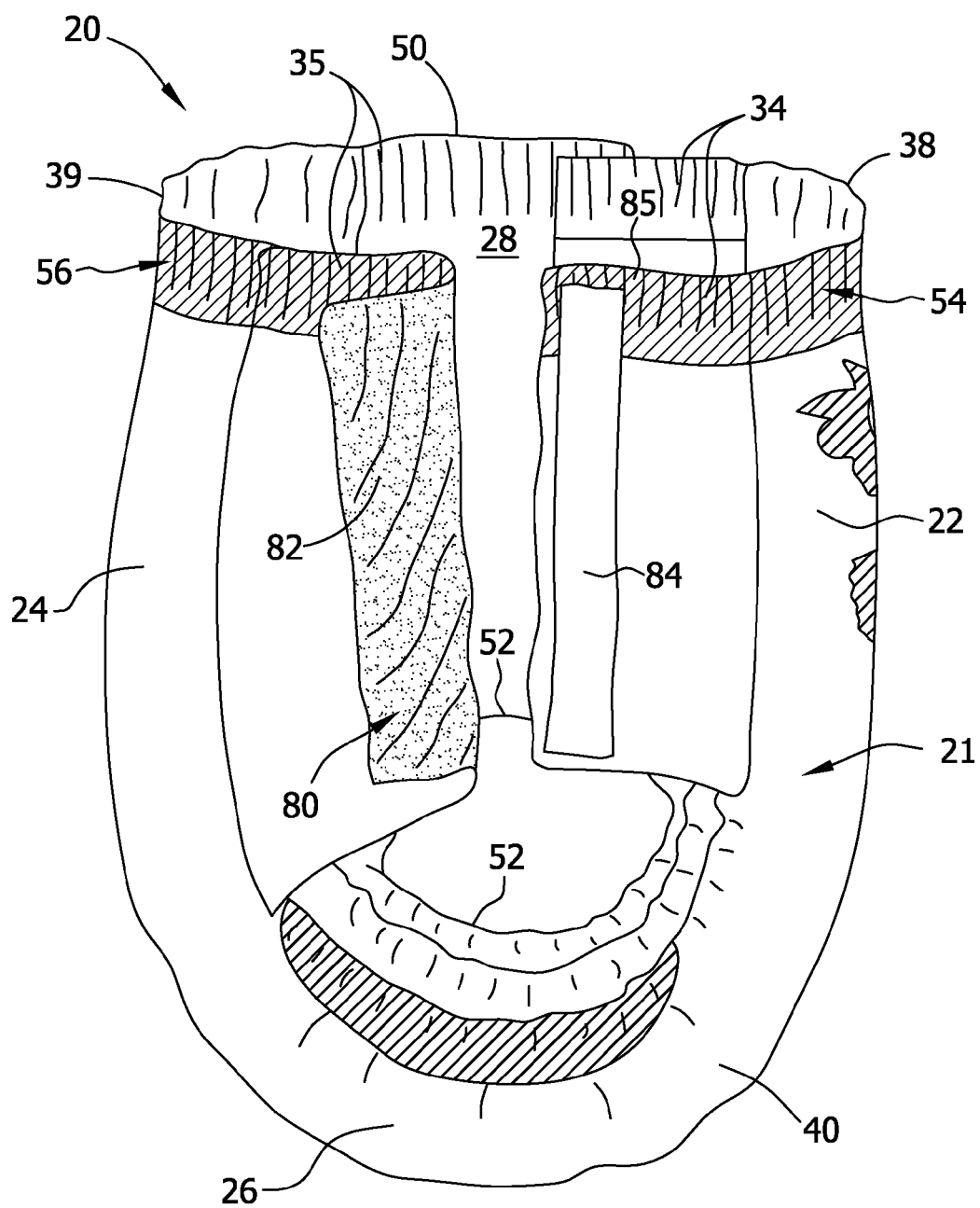
FIG. 1 is a perspective of one embodiment of an absorbent article in the form of a training pant having a mechanical fastening system in a partially fastened configuration.
Figure 2:
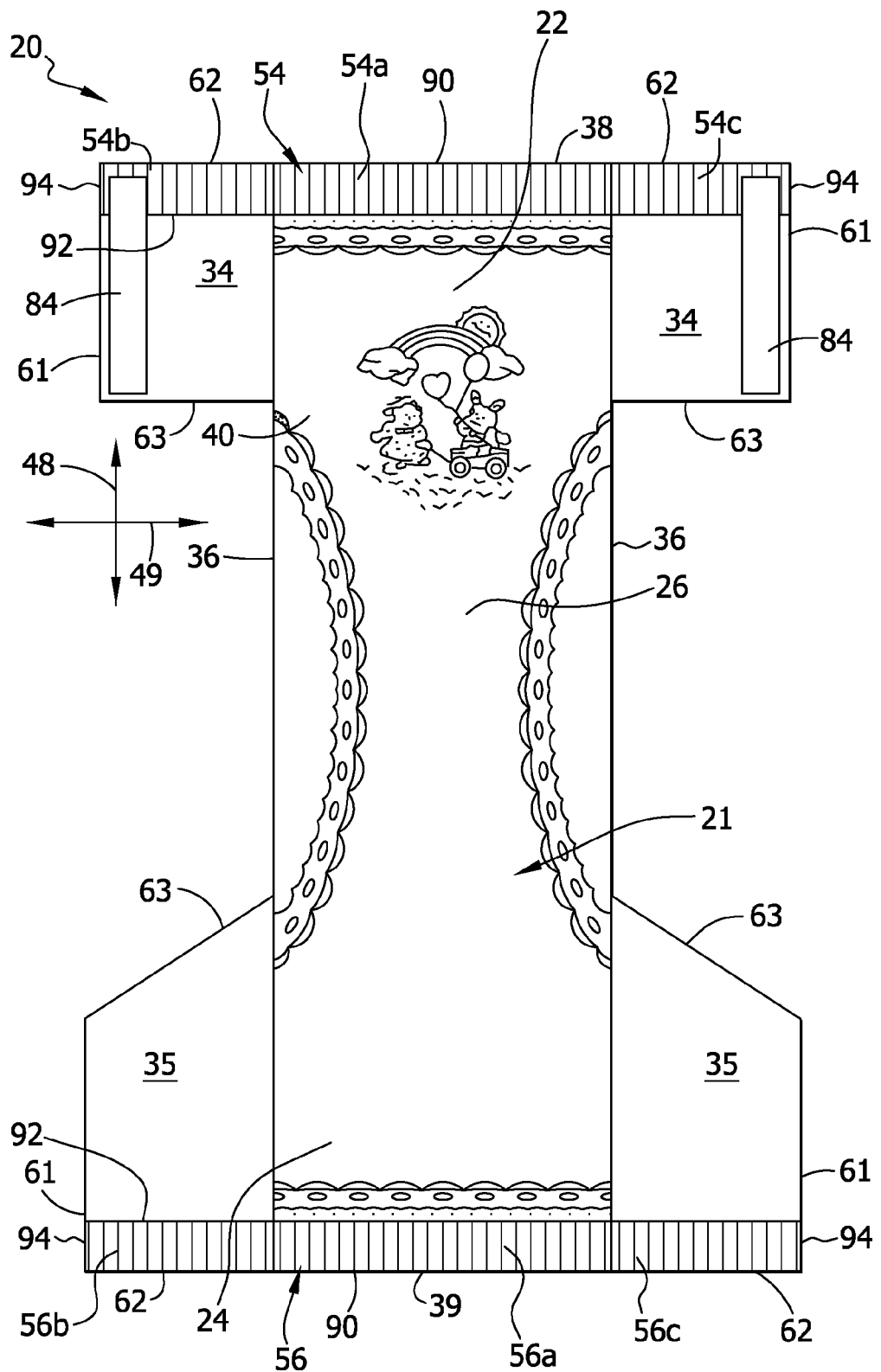
FIG. 2 is a plan view of the training pant in an unfastened, unfolded and laid flat condition, and showing the surface of the training pant that faces away from a wearer during use.
Figure 3:
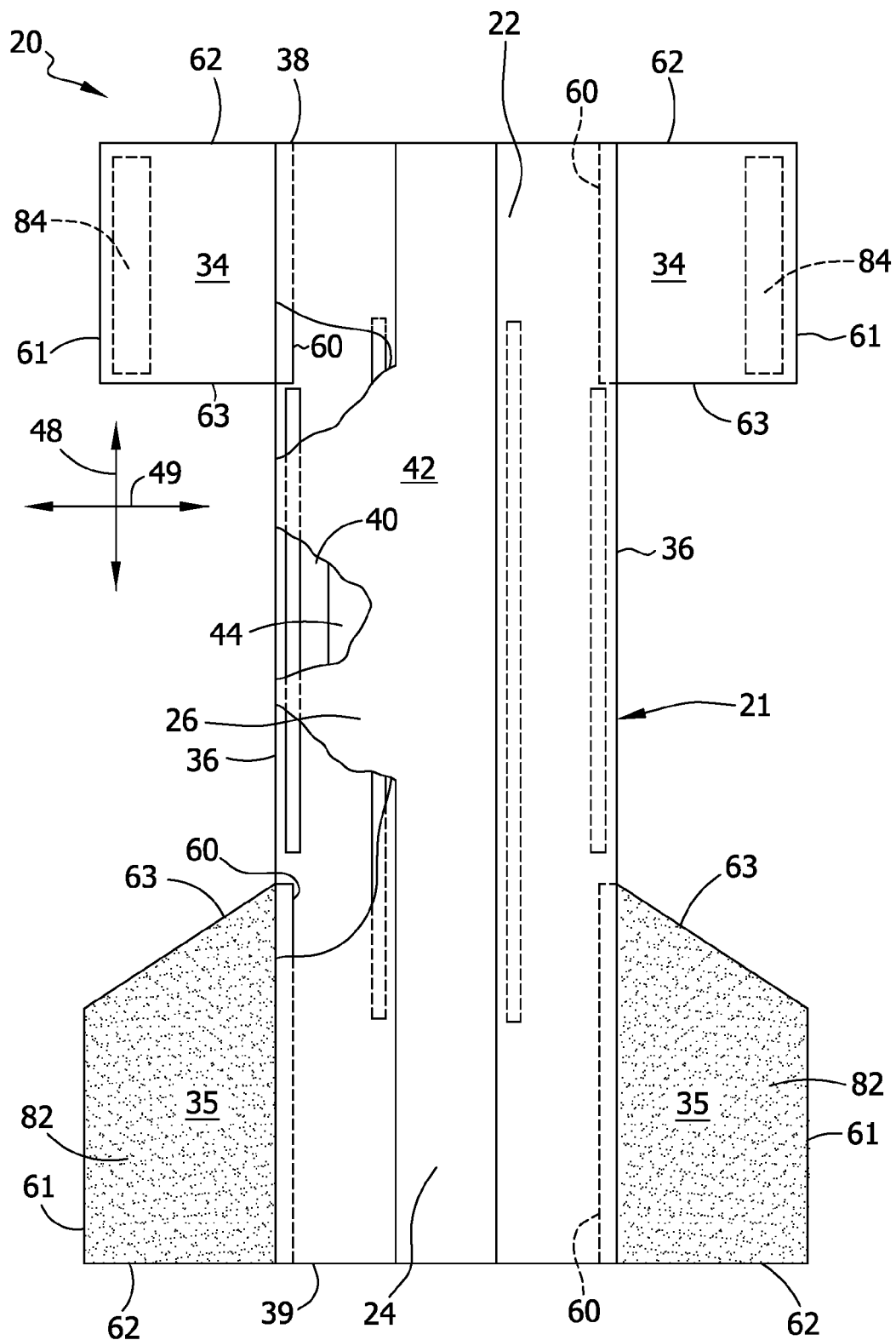
FIG. 3 is a plan view of the training pant in an unfastened, unfolded and laid flat condition, and showing the surface of the training pant that faces the wearer during use, portions of the training pant being cut away to show underlying components.

With reference now to the drawings, FIGS. 1-3 illustrated an absorbent article in the form of a training pant, which is indicated generally by reference number 20. The training pant 20 comprises a generally rectangular chassis, indicated at 21, a pair of laterally opposite front side panels 34, and a pair of laterally opposite back side panels 35. For reference, arrows 48 and 49 depict the orientation of the longitudinal axis and the transverse or lateral axis, respectively, of the training pant 20 (FIGS. 2 and 3). It is contemplated that the absorbent article can have other forms without departing from some aspects of this invention (e.g., a diaper, an incontinence article, swim wear).

The chassis 21 of the training pant 20 is configured to contain and/or absorb exudates released by a wearer during use of the training pant. As seen in FIG. 2, the chassis 21 has a front waist region 22, a back waist region 24, and a crotch region 26 extending between and interconnecting the front and back waist regions. The chassis 21 further includes a pair of side edges 36, a front waist edge 38, and back waist edge 39.

With reference now to FIG. 3, the illustrated chassis 21 comprises an outer cover 40, a body-side liner 42, and an absorbent assembly 44 disposed between the outer cover and the body-side liner. In one suitable embodiment, the outer cover 40 comprises a material that is substantially liquid impermeable, and can be elastic, stretchable, or nonstretchable. The outer cover 40 can be a single layer of liquid impermeable material, but suitably comprises a multi-layered laminate structure in which at least one of the layers is liquid impermeable. For instance, the outer cover 40 can include a liquid permeable outer layer and a liquid impermeable inner layer that are joined together by a laminate adhesive, ultrasonic bonds, thermal bonds, or the like. Suitable laminate adhesives can be applied continuously or intermittently as beads, a spray, parallel swirls, or the like. The liquid permeable outer layer can be any suitable material and desirably one that provides a generally cloth-like texture. The inner layer of the outer cover 40 can be both liquid and vapor impermeable, or can be liquid impermeable and vapor permeable. The inner layer can be manufactured from a thin plastic film, although other flexible liquid impermeable materials may also be used. The inner layer, or the liquid impermeable outer cover 40 when a single layer, inhibits liquid exudates from wetting articles, such as bed sheets and clothing, as well as the wearer.

The body-side liner 42 is liquid permeable and overlies the absorbent assembly 44 and outer cover 40. Thus, the body-side liner 42 defines a bodyfacing surface of the training pant 20, which is compliant, soft feeling, and non-irritating to the wearer's skin. Further, the body-side liner 42 may be less hydrophilic than the absorbent assembly 44, to present a relatively dry surface to the wearer, and may be sufficiently porous to be liquid permeable, permitting liquid to readily penetrate through its thickness. Suitable body-side liners 42 can be manufactured from a wide selection of web materials, such as porous foams, reticulated foams, apertured plastic films, natural fibers (i.e., wood or cotton fibers), synthetic fibers (i.e., polyester or polypropylene fibers), or a combination of natural and synthetic fibers. The body-side liner 42 is suitably employed to help isolate the wearer's skin from liquids held in the absorbent assembly 44.

The body-side liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the body-side liner 42. For example, the body-side liner 42 can be composed of a meltblown or spunbonded web of polyolefin fibers. The body-side liner can also be a bonded-carded web composed of natural and/or synthetic fibers. The body-side liner can be composed of a substantially hydrophobic material, and the hydrophobic material can, optionally, be treated with a surfactant or otherwise processed to impart a desired level of wettability and hydrophilicity. In one suitable embodiment, for example, the body-side liner 42 can be a hydrophobic three-layer nonwoven polypropylene material known as SMS. SMS is an acronym for Spunbond, Meltblown, Spunbond, the process by which the three layers are constructed and then laminated together. One example of an SMS material is described in U.S. Pat. No. 4,041,203 to Brock et al.

The absorbent assembly 44 is generally compressible, conformable, non-irritating to the wearer's skin, and capable of absorbing and retaining liquids and certain other body exudates. The absorbent assembly 44 can be manufactured in a wide variety of sizes and shapes, and from a wide variety of liquid absorbent materials commonly used in the art. For example, the absorbent assembly 44 can suitably comprise a matrix of hydrophilic fibers, such as a web of cellulosic fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Typically, a superabsorbent material is capable of absorbing at least about 15 times its weight in water, and desirably is capable of absorbing more than about 25 times its weight in water. As a general rule, the superabsorbent material is present in the absorbent assembly 44 in an amount of from 0 to about 90 percent weight based on total weight of the absorbent assembly. The absorbent assembly 44 may or may not be wrapped or encompassed by a suitable tissue wrap that may help maintain the integrity and/or shape of the absorbent assembly.

The chassis 21 can also incorporate other materials designed primarily to receive, temporarily store, and/or transport liquid along the mutually facing surface with absorbent assembly 44, thereby maximizing the absorbent capacity of the absorbent assembly. One suitable material is referred to as a surge management layer (not shown) and may be located adjacent the absorbent assembly 44 (e.g., between the absorbent assembly and the liner 42). The surge management layer helps to decelerate and diffuse surges or gushes of liquid that may be rapidly introduced into the absorbent assembly 44. The surge management layer can rapidly accept and temporarily hold the liquid prior to releasing the liquid into the storage or retention portions of the absorbent assembly 44. Examples of suitable surge management layers are described in U.S. Pat. Nos. 5,486,166 and 5,490,846. Other suitable surge management materials are described in U.S. Pat. No. 5,820,973.

As seen in FIGS. 2 and 3, the front and back side panels 34, 35 are disposed on laterally opposite sides of the absorbent structure 33 in longitudinally spaced relationship with each other. In the illustrated embodiment, the front and back side panels 34, 35 are permanently bonded along seams to the chassis 21 in the respective front and back waist regions 22, 24. More specifically, each of the front and back side panels 34, 35 are sandwiched between the outer cover 40 and the body-side liner 44 and permanently bonded to both the outer cover and the body-side liner. The front side panels 34 extend transversely outward beyond the side edges 36 of the chassis 21 in the front waist region 22, and the back side panels 35 extend transversely outward beyond the side edges of the chassis in the back waist region 24.

The front and back side panels 34, 35 can be bonded to the chassis 21 using attachment means known to those skilled in the art such as adhesive, thermal or ultrasonic bonding, or combinations thereof. In the illustrated embodiment, for example, the front and back side panels 34, 35 are thermally or ultrasonically bonded to both the outer cover 40 and the body-side liner 44.

As seen in FIG. 3, each of the front and back side panels 34, 35 have a proximal edge 60, a distal edge 61, a waist opening edge 62, and a leg opening edge 63. The proximal edge 60 is the edge of the respective side panel 34, 35 that is joined to the chassis 21. The distal edge 61 is opposite the proximal edge 60 and spaced from the chassis 21. The waist opening edge 62 and the leg opening edge 63 extend between the proximal and distal edges 60, 61.

In the illustrated embodiment, the proximal edge 60 and the distal edge 61 of each of the front and back side panels 34, 35 are generally straight and parallel to each other. It is understood, however, that the proximal edges 60 and the distal edges 61 of the front side panels 34 and/or back side panels 35 can be other than straight (e.g., curved). It is also understood that the proximal edges 60 and the distal edges 61 of the front side panels 34 and/or back side panels 35 can be nonparallel.

The waist opening edges 62 of both the front and back side panels 34, 35 are generally straight and perpendicular to the proximal edges 60 and the distal edges 61. As seen in FIGS. 2 and 3, the waist opening edges 62 of the front side panel 34 are generally aligned with the front waist edge 38 of the chassis 21, and the waist opening edges of the back side panel 35 are generally aligned with the back waist edge 39 of the chassis.

With reference still to FIGS. 2 and 3, the leg opening edges 63 of the front side panels 34 are generally straight, parallel the waist opening edge 62, and perpendicular to the proximal and distal edges 60, 61. It is understood, however, that the leg opening edge 63 of each of the front side panels 34 can be other than straight. In one suitable embodiment having non-straight leg openings edges 63 of the front side panels 34, for example, the leg opening edges can be convexly or concavely arcuate.

The leg opening edges 63 of the illustrated back side panels 35 are straight but angled along their respective length. That is, the leg opening edges 63 of the back side panels are nonparallel to the respective waist opening edge 62. It is contemplated, however, that the leg opening edges 63 of each of the back side panels 35 can have other shapes. For example, the leg opening edges can be non-straight (e.g., concavely or convexly arcuate).

In one suitable embodiment, the front and back side panels 34, 35 comprise an elastic material capable of stretching in at least a direction generally parallel to the transverse axis 49 of the training pant 20. Suitable elastic materials, as well as one process of incorporating elastic side panels into training pant, are described in U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.

In particular embodiments, the elastic material comprises a stretch-thermal laminate (STL), a neck-bonded laminate (NBL), a reversibly necked laminate, a stretch-bonded laminate (SBL) material. Methods of making suitable elastic materials are well known to those skilled in the art and described, for example, in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the names of Taylor et al.; and U.S. Pat. No. 7,803,244 issued on Sep. 28, 2010 to Siqueira et al. Alternatively, the side panel material may comprise other woven or nonwoven materials, such as those described above as being suitable for the outer cover 40 or body-side liner 42, mechanically pre-strained composites, or stretchable but inelastic materials.

The illustrated training pant 20 includes a fastening system 80 for refastenably securing the training pant about a waist of the wearer. The illustrated fastening system 80 includes first fastening components 84 adapted for refastenable engagement to corresponding second fastening components 82. In the illustrated embodiment, the first fastening components 84 comprise a plurality of projecting engaging elements. The engaging elements of the first fastening components 84 are adapted to repeatedly engage and disengage engaging elements of the second fastening components 82.

The fastening components 84, 82 can comprise separate elements bonded to the side panels 34, 35, or they may be integrally formed with the side panels. In the illustrated embodiment, for example, the first fastening components 84 are formed separate from the front side panels 34 and bonded thereto. The second fastening components 82, on the other hand, are integrally formed with the back side panels 35. The first fastening components 84 can be bonded to the respective front side panels 34 by any means known to those skilled in the art such as adhesive bonds, ultrasonic bonds or thermal bonds.

The fastening components 84, 82 can comprise any refastenable fasteners suitable for absorbent articles, such as adhesive fasteners, cohesive fasteners, mechanical fasteners, or the like. In the illustrated embodiment, the fastening components 84, 82 comprise mechanical fastening elements. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated embodiment, the first fastening components 84 comprise hook fasteners and the second fastening components 82 comprise complementary loop fasteners. In another suitable embodiment, the first fastening components 84 comprise loop fasteners and the second fastening components 82 comprise complementary hook fasteners. Alternatively, the fastening components 84, 82 may comprise interlocking similar surface fasteners, adhesive or cohesive fastening elements such as an adhesive fastener and an adhesive-receptive landing zone or material; or the like.

In a ready-to-wear, three dimensional configuration of the training pant 20, the front and back side panels 34, 35 are secured together to define a three-dimensional pants configuration having a waist opening 50 and a pair of leg openings 52 (FIG. 1). The front waist region 22 comprises the portion of the training pants which, when worn, is positioned on the front of the wearer while the back waist region 24 comprises the portion of the training pants which, when worn, is positioned on the back of the wearer. The crotch region 26 of the training pant 20 comprises the portion of the training pants which, when worn, is positioned between the legs of the wearer and covers the lower torso of the wearer. The front and back side panels 34, 35 define the portions of the training pant 20 which, when worn, are positioned on the hips of the wearer.

As seen in FIG. 1, in the ready-to-wear, three dimensional configuration of the training pant 20, the back side panels 35 overlap the front side panels 34 when the first fastening component 84 is and the second fastening component 82 is engaged. It is understood, however, that the training pant 20 may instead be configured so that the front side panels 34 overlap the back side panels 35.

In another suitable embodiment (not shown), the front and back side panels 34, 35 can be permanently bonded together. In such an embodiment, the fastening system 80 is omitted and each of the front side panels 34 is permanently bonded to the respective back side panel 35.

With reference now to FIGS. 1 and 2, the training pant 20 includes a front waist elastic member 54, and a rear waist elastic member 56. The waist elastic members 54, 56 can be formed of any suitable elastic material. Exemplary suitable elastic materials include sheets, strands or ribbons of natural rubber, synthetic rubber, or thermoplastic elastomeric polymers.

In the illustrated embodiment, both the front and back waist elastic members 54, 56 are generally rectangular in shape having a top edge 90, a bottom edge 92, and two side edges 94. As seen in FIG. 2, the top edges 90 of the front and back waist elastic members 54, 56 of the illustrated embodiment are generally aligned with the front waist edge 38 and back waist edge 39, respectively, of the outer cover 40. In addition, the top edges 90 of the front and back waist elastic members 54, 56 are aligned with of the waist opening edges 62 of the respective side panels 34, 35. It is understood, however, that the top edges 90 of the front waist elastic member 54 and/or the back waist elastic member 56 can be spaced from the front waist edge 38 of the chassis 21, the back waist edge 39 of the chassis, and/or waist opening edges 62 of the front and back side panels 34, 35. That is, the top edges 90 of the front waist elastic member 54 and/or the back waist elastic member 56 can be spaced either above or below the front waist edge 38 of the chassis 21, the back waist edge 39 of the chassis, and/or the waist opening edges 62 of the front and back side panels 34, 35.

As illustrated in FIG. 2, each of the side edges 94 of the front and back waist elastic members 54, 56 are generally aligned with the distal edges 61 of the front and back side panels 34, 35. It is understood, however, that the side edges 94 of the front and/or back waist elastic members 54, 56 can be disposed either outward or inward of the distal edges 61 of the front and back side panels 34, 35. In one suitable embodiment, for example, the side edges 94 of the front waist elastic member 54 can terminate adjacent to or in abutting relationship with the first fastening components 84, which are located on the front side panels 34.

In the illustrated embodiment, each of the front and back waist elastic members 54, 56 comprises three segments. Central segments 54a, 56a of the front and back waist elastic members 54, 56 are attached to the chassis 21, and lateral segments 54b, 54c, 56b, 56c are attached to respective front or back side panels 34, 35. In the illustrated embodiment, portions of the central segments 54a, 56a overlie portions of the lateral segments 54b, 54c, 56b, 56c. It is contemplated, however, that portions of the lateral segments 54b, 54c, 56b, 56c could overlie portions of the central segments 54a, 56a. It is also contemplated that the central segments 54a, 56a and the lateral segments 54b, 54c, 56b, 56c can be arranged in end-to-end, abutting and non-overlapping relationship.

In one suitable embodiment and explained in more detail below, the front and back waist elastic members 54, 56 are point bonded to the absorbent chassis 21 and the respective front and back side panels 34, 35 using a plurality of point bond. In one configuration, the point bonds are generally aligned in longitudinally extending rows with each of the rows being generally uniformly spaced apart, which provides uniform gathers in the front and back waist elastic members 54, 56.

While the bond points can have various sizes and shape, in one suitable configuration, the bond points are generally circular and have a diameter of less than about 10 millimeters and suitably, between about 0.5 millimeters and about 3 millimeters. For example, the bond points can have a diameter of approximately 1 millimeter. It is understood, however, that the bond points can have any suitable size or shape.

Figure 4:
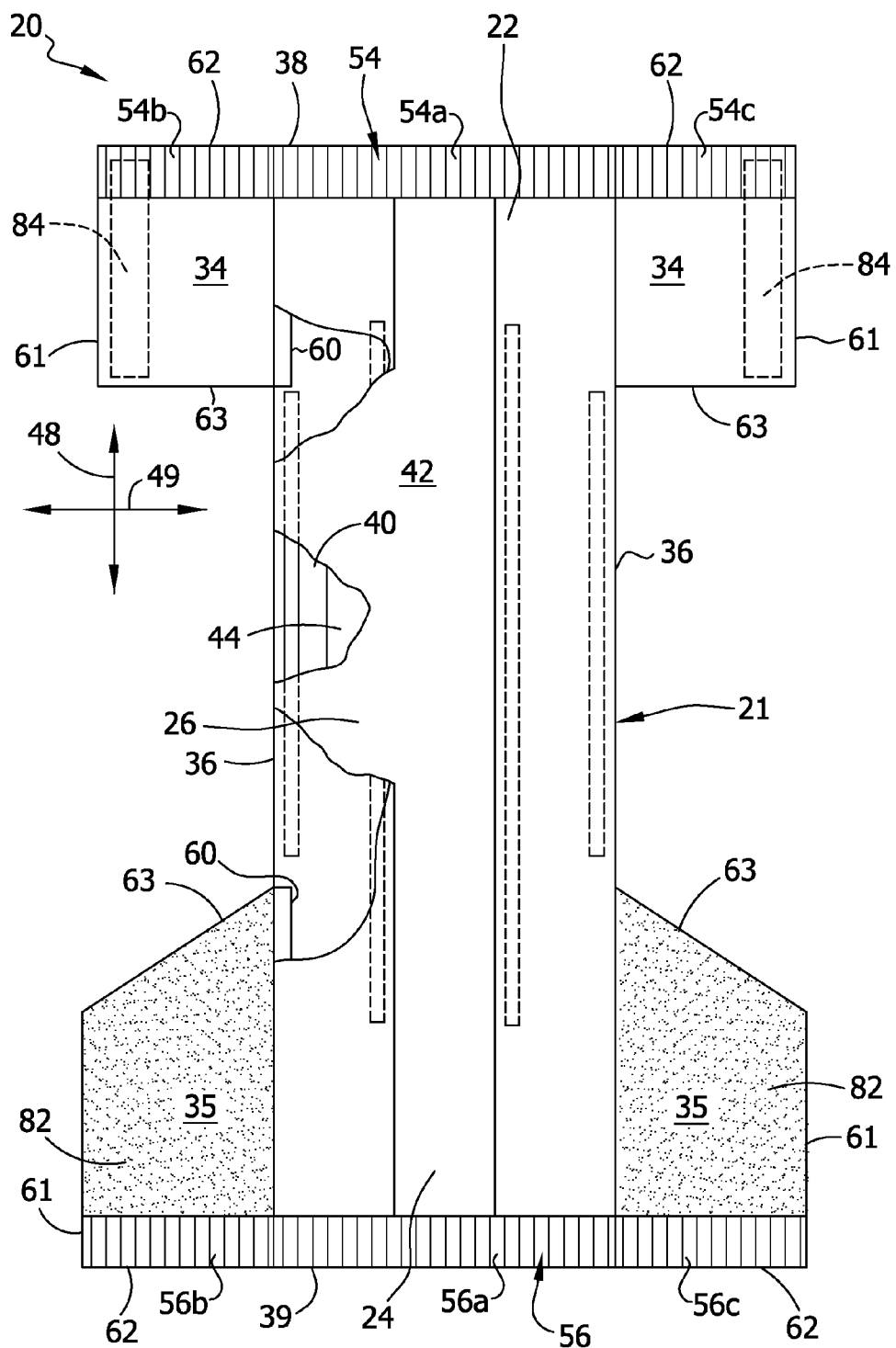
FIG. 4 is a plan view of another embodiment of an absorbent article in the form of a training pant in an unfastened, unfolded and laid flat condition, and showing a surface of the training pant that faces a wearer during use, portions of the training pant being cut away to show underlying components.
Figure 5:
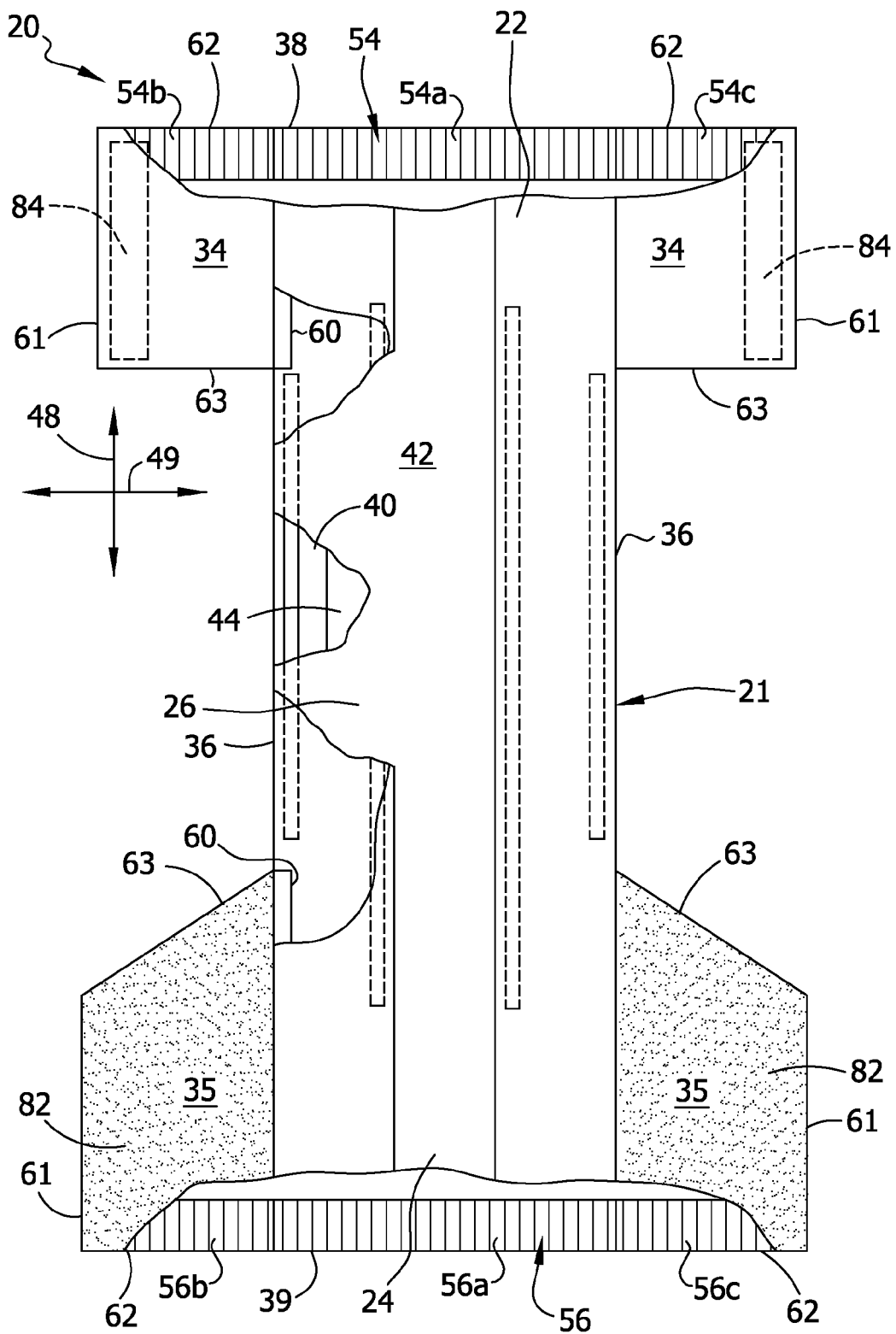
FIG. 5 is a plan view of yet another embodiment of an absorbent article in the form of a training pant in an unfastened, unfolded and laid flat condition, and showing a surface of the training pant that faces a wearer during use, portions of the training pant being cut away to show underlying components.

In one suitable embodiment and as seen in FIG. 3, the front and back waist elastic members 54, 56 are disposed on the outer cover 40. Thus, during use of the training pants 20, the front and back waist elastic members 54, 56 are readily visible. It is contemplated, however, that the front waist elastic member 54 and/or the back waist elastic member 56 can be disposed on the body-side liner 42 such that the elastic member faces the wearer during use as illustrated in FIG. 4. It is also contemplated that the front waist elastic member 54 and/or the back waist elastic member 56 can be disposed between the body-side liner 42 and the outer cover 40 as illustrated in FIG. 5.

In one suitable embodiment, the presence or noticeability of the front waist elastic member 54 and/or the back waist elastic member 56 can be enhanced by providing suitable visual and/or tactile cues (e.g., graphics, texturing) on the waist elastic member(s). The visual and/or tactile cues can be provided to increase the noticeability that the front and back waist elastic members 54, 56 cooperate during use to fully encircle the waist of the wearer. In the illustrated embodiment, for example, both the front and back waist elastic members 54, 56 are a different color than the chassis 21 and side panels 34, 35 (see FIG. 1).

Figure 6:
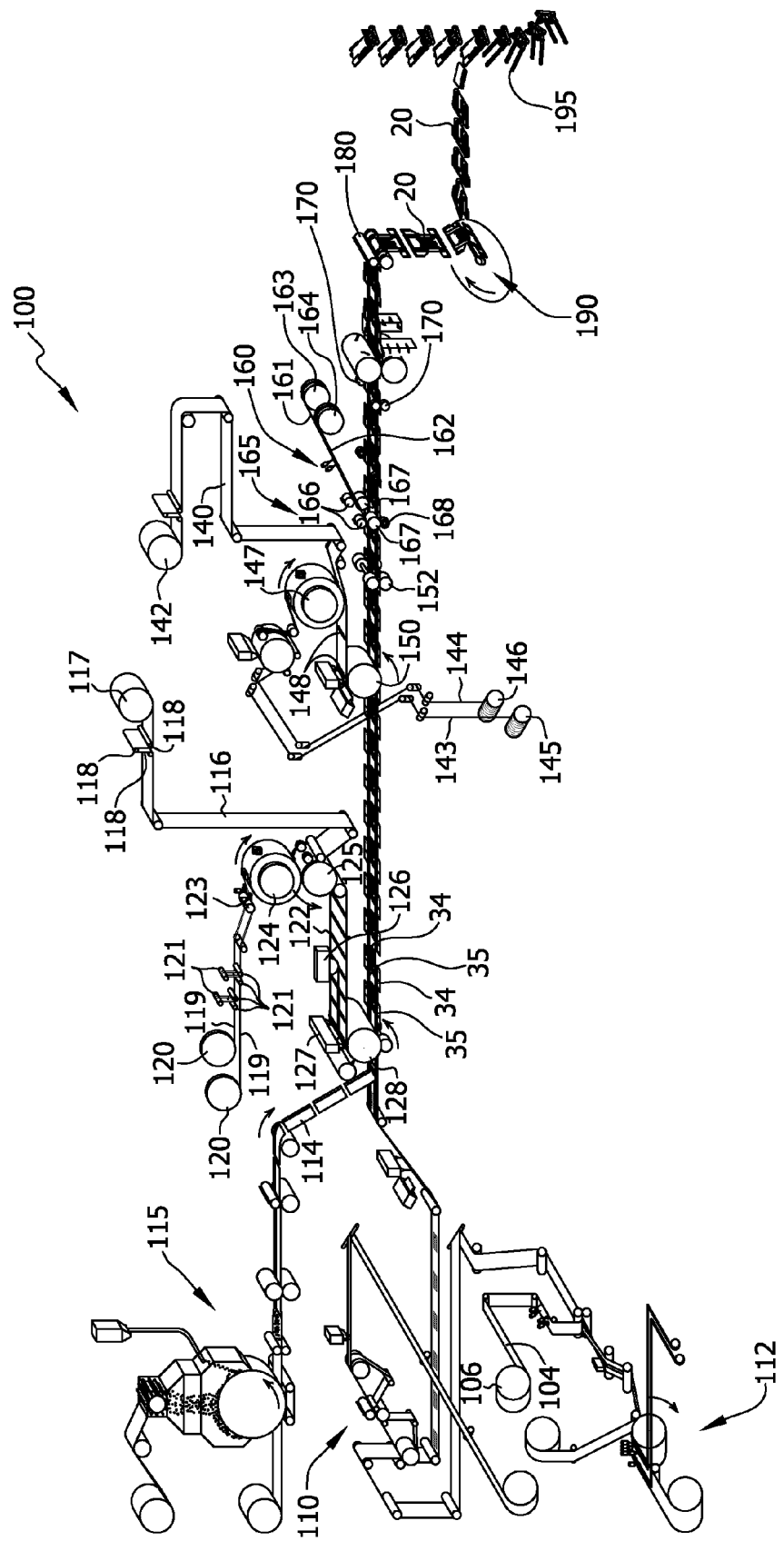
FIG. 6 is a schematic illustrating one suitable method for manufacturing the training pant of FIGS. 1-3 wherein a web of suitable side panel material is stretched in a cross-machine direction and two continuous webs of suitable waist elastic material are stretched in a machine direction.

FIG. 6 schematically illustrates one suitable apparatus 100 for manufacturing the training pant 20 illustrated in FIGS. 1-3. As seen in FIG. 6, a continuous supply of material 104 used to form the liner 42 is provided from a suitable supply source 106. Various components of the training pant 20 can be disposed on and/or bonded to the bodyside liner material 104 as the material travels in a machine direction. In particular, a surge layer can be provided at an application station, indicated generally at 110, and disposed on and/or bonded to the bodyside liner material 104. Additionally, a containment flap module, indicated generally at 112, can be provided downstream of the supply source 106 for attaching pre-assembled containment flaps to the bodyside liner material 104.

A plurality of absorbent assemblies 114 can be provided from a suitable supply source, indicated generally at 115. The supply source 115 can be any conventional mechanism for supplying the absorbent assemblies 114. Generally, a conventional supply source can include a hammermill for forming fluff fibers and, if desired, an enclosure for mixing superabsorbent material with the fluff fibers, and a forming drum having a desired absorbent design. The individual absorbent assemblies 114 can be disposed intermittently on the continuously moving bodyside liner material 104, one for each training pant 20. In the illustrated embodiment, the position of the absorbent assemblies 114 is registered with the position of the surge material. The absorbent assemblies 114 can be bonded to one or more other components using adhesives or other suitable means.

A continuous web of material 116 used to form the side panels 34, 35 is provided from a suitable supply source 117. The supply source 117 can comprise any suitable mechanism. In the illustrated embodiment, the continuous web of material 116, which is capable of stretching in at least the cross-machine direction, is driven past a plurality of rollers 118.

Two continuous webs of suitable waist elastic material 119 used to form the lateral segments 54b, 54c, 56b, 56c of the front and back waist elastic members 54, 56 are provided by suitable supply sources 120. While two supply sources 120 are illustrated in FIG. 6, it is understood that more or fewer (i.e., one) supply sources can be used. Each of the webs of waist elastic material 119 is stretched in the machine direction using a plurality of tensioning rolls 121.

In the illustrated embodiment, each of the webs of waist elastic material 119 are cut at a cutting station 123 to form a plurality of discrete pieces 122 of waist elastic material. The discrete pieces 122 are maintained in a stretched configuration, oriented with respect to the web of side panel material 116 at an orientation station 124, and bonded to the web of side panel material at a bonding station 125. In the illustrated embodiment, the discrete pieces 122 are oriented generally in the cross-machine direction before being bonded to the web of side panel material 116, which is traveling in the machine direction. The discrete pieces 122 of waist elastic material can be bonded to the side panel material 116 at the bonding station 125 using any suitable bonding technique. In one suitable embodiment, the discrete pieces of waist elastic material 122 are point bonded to the web of side panel material 116 using pressure, adhesive, thermal and/or ultrasonic bonding.

With the discrete pieces of waist elastic material 122 bonded to the web of side panel material 116, the web of side panel material is cut in the machine direction by a slitter 126 aligned generally with a centerline of the web to form two continuous webs. The web of side panel material 116 is then cut in the cross-machine direction a cutting station 127 to form a plurality of side panels 34, 35.

As seen in FIG. 6, the side panels 34, 35 are orientated with respect to and positioned in partially overlapping relationship with the bodyside liner material 104 using a suitable applicator device 128. In the cross-machine direction, each of the side panels 34, 35 extends laterally outward from the bodyside liner material 104 and overlaps the bodyside liner material by a suitable amount to permit bonding of the side panels to the bodyside liner.

With reference still to FIG. 6, a continuous supply of material 140 used to form the outer cover 40 is provided from a suitable supply source 142. The central segments 54a, 56a of the front and back waist elastic members 54, 56 are attached to the outer cover material 40 as the outer cover material travels in the machine direction. More specifically, two continuous webs 143, 144 of waist elastic material are feed from suitable supply sources 145, 146. The waist elastic material webs 143, 144 are cut into segments 148, the segments are oriented in a cross-machine direction, and bonded to the outer cover material 140 at a cutting, orienting, and bonding station 147.

The outer cover material 140, which has the central segments 54a, 56a of the front and back waist elastic members 54, 56 attached thereto, is transported over a laminator roll 150 and joined to the bodyside liner material 104. The absorbent assemblies 114 are thereby sandwiched between the continuous bodyside liner and outer cover materials 104, 140. The inward portions of the side panels 34, 35 is also disposed between the bodyside liner material 104 and the outer cover material 140. The lateral segments 54b, 54c, 56b, 56c of the front and back waist elastic members 54, 56, which are bonded to the front and back side panels 34, 35, are generally aligned with the respective central segments 54a, 56a of the front and back waist elastic members 54, 56, which are bonded to the chassis.

A bonding device 152, such as an ultrasonic bonder, is located downstream of the laminator roll 150 to bond the bodyside liner material 104, side panels 34, 35 and outer cover material 140 together. For example, these materials can be collectively transported between a rotary ultrasonic horn and an anvil roll adapted to point bond the bodyside liner material 104, side panels 34, 35 and outer cover material 140 together.

Next in the illustrated embodiment, a fastener application station, indicated generally at 160, attaches the first fastening components 84 to the front side panels 34. In the illustrated embodiment, the second fastening components 85 are formed integrally with the back side panels 35 but it is contemplated that the second fastening components can be formed separately from the back side panels and bonded thereto at the fastener application station 160.

As seen in FIG. 6, continuous webs of first fastener material 161, 162 used to form the first fastening components 84 is provided from suitable supply sources 163, 164. The first fastener materials 161, 162 is cut into individual first fastener components 84 at cutting assembly, indicated generally at

165. The illustrated cutting assembly 165 includes rotatable knife rolls 166, rotatable vacuum anvil rolls 167, and rotatable backing rolls 168. Only one backing roll 168 is illustrated in FIG. 6. Thus, the continuous first fastener materials 161, 162 is cut by blades on the knife rolls 166, maintained on the anvil rolls 167 by vacuum, and placed on the front side panels 34. After the first fastening components 84 are disposed on the front side panels 34, suitable bonding devices 170, such as ultrasonic bonders, can be used to bond the first fastening components to the front side panels.

A cutter 180 selectively cuts the web into discrete, partially assembled training pants 20. Such cutters 180 are generally known to those skilled in the art and can include, for example, the combination of a cutting roll and an anvil roll through which the web travels. The discrete training pants 20 are then folded at a folding station, indicated generally at 190, using a suitable folding mechanism (e.g., blade folders, linear folders, book folders, tucker blades). In one suitable configuration, the training pants 20 are folded about a fold line generally bisecting the training pants. As such, the front and back waist regions 22, 24 of each training pant 102 are positioned in facing relationship with the side panels 34, 35 extending laterally outward relative to the longitudinal axis 48 of the training pant. The fold line extends generally about the transverse axis 49 of the training pant through the crotch region 26. Once the training pants 20 are folded they can be stacked, such as by a suitable stacking apparatus 195, and packaged.

Figure 7:
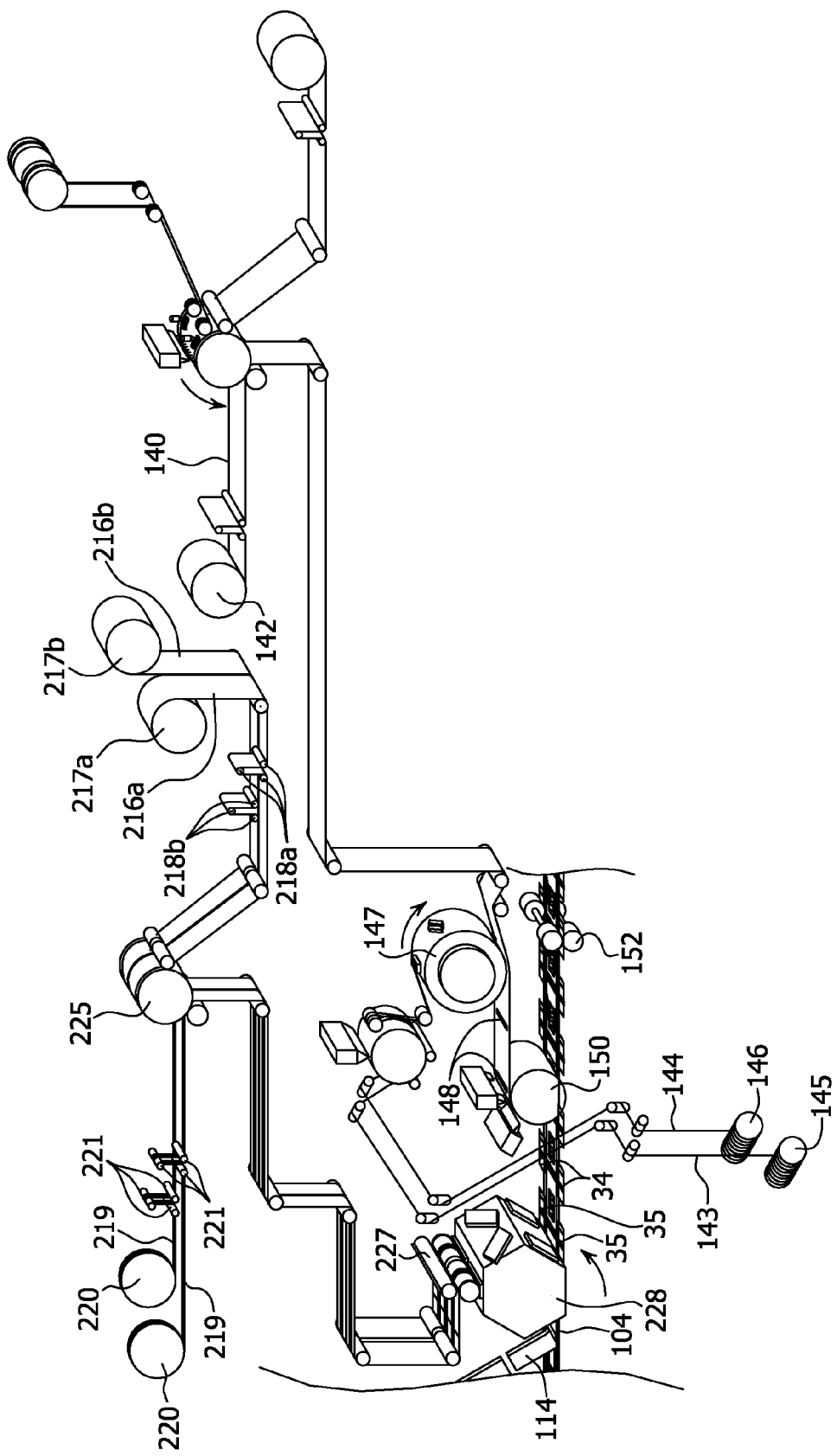
FIG. 7 is a schematic illustrating one suitable method for attaching side panels during the manufacturing of the training pant wherein two continuous webs of suitable side panel material are stretched in a machine direction and two continuous webs of suitable waist elastic material are stretched in a machine direction.

FIG. 7 illustrates another suitable method for attaching the side panels 34, 35 during the manufacturing of the training pant 20. As seen therein, two continuous webs of material 216a, 216b used to form the side panels 34, 35 are provided from suitable supply sources 217a, 217b. Each of the web of side panel materials 216a, 216b is stretched longitudinally in a machine direction using a plurality of tensioning rolls 218a, 218b as the web is being feed in the machine direction.

Two continuous webs of suitable waist elastic material 219 used to form the lateral segments 54b, 54c, 56b, 56c of the front and back waist elastic members 54, 56 are provided by suitable supply sources 220. Each of the webs of waist elastic material 219 is stretched in the machine direction using a plurality of tensioning rolls 221. Each of the webs of waist elastic material 219 is bonded to one of the webs of side panel material 216a, 216b at a bonding station 225. As seen in FIG. 7, the webs of waist elastic material 219 are oriented generally in the machine direction as they are being bonded to the respective web of side panel material 216a, 216b, which is also traveling in the machine direction. The webs of waist elastic material 219 can be bonded to the webs of side panel material 216a, 216b at the bonding station 225 using any suitable bonding technique. In one suitable embodiment, the webs of waist elastic material 219 are point bonded to the webs of side panel material 216a, 216b using pressure, adhesive, thermal and/or ultrasonic bonding.

With the webs of waist elastic material 219 bonded to the webs of side panel material 216a, 216b, the webs of side panel material are cut in the cross-machine direction a cutting station 227 to form a plurality of side panels 34, 35. Each of the side panels 34, 35 is allowed to relax. That is, the stretch, which was maintained in both the side panel material and the waistband material during the formation of the side panels 34, 35 is released allowing the side panels to retract to an unstrained position.

With the side panels 34, 35 in the unstrained position (i.e., relaxed), the side panels are orientated with respect to and positioned in partially overlapping relationship with the bodyside liner material 104 using a suitable applicator device 228. Each of the side panels 34, 35 extends laterally outward from the bodyside liner material 104 in the cross-machine direction and overlaps the bodyside liner material by a suitable amount to permit bonding of the side panels to the bodyside liner.

As seen in FIG. 7, a continuous supply of material 140 used to form the outer cover 40 is provided from a suitable supply source 142. The central segments 54a, 56a of the front and back waist elastic members 54, 56 are attached to the outer cover material 40 as the outer cover material travels in the machine direction. More specifically, two continuous webs 143, 144 of waist elastic material are feed from suitable supply sources 145, 146. The waist elastic material webs 143, 144 are cut into segments 148, the segments are oriented in a cross-machine direction, and bonded to the outer cover material 140 at a cutting, orienting, and bonding station 147.

The outer cover material 140, which has central segments 54a, 56a of the front and back waist elastic members 54, 56 attached thereto, is transported over a laminator roll 150 and joined to the bodyside liner material 104. The absorbent assemblies 114 are thereby sandwiched between the continuous bodyside liner and outer cover materials 104, 140. The inward portions of the of the side panels 34, 35 is also disposed between the bodyside liner material 104 and the outer cover material 140.

A bonding device 152, such as an ultrasonic bonder, is located downstream of the laminator roll 150 to bond the bodyside liner material 104, side panels 34, 35 and outer cover material 140 together. For example, these materials can be collectively transported between a rotary ultrasonic horn and an anvil roll adapted to point bond the bodyside liner material 104, side panels 34, 35 and outer cover material 140 together.

Figure 8:
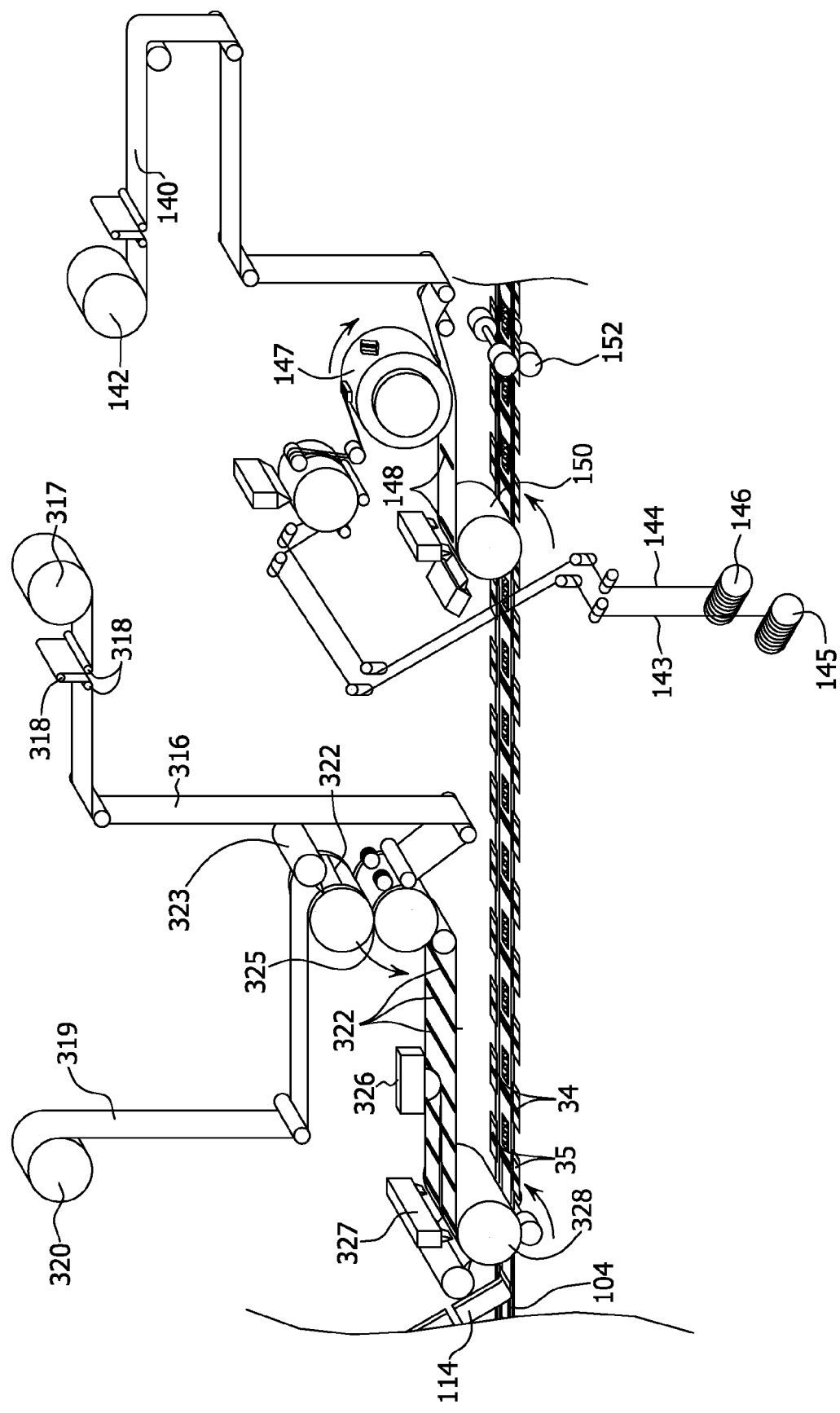
FIG. 8 is a schematic illustrating another suitable method for attaching side panels during the manufacturing of the training pant wherein a web of suitable side panel material is stretched in a cross-machine direction and a web of suitable waist elastic material is stretched in a cross-machine direction.

FIG. 8 illustrates yet another suitable method for attaching the side panels 34, 35 during the manufacturing of the training pants. As illustrated in FIG. 8, a continuous web of material 316 used to form the side panels 34, 35 is provided from a suitable supply source 317. The web of side panel material 316, which is capable of stretching in at least the cross-machine direction, is driven past a plurality of rollers 318. In addition, a continuous web of suitable waist elastic material 319 used to form the lateral segments 54b, 54c, 56b, 56c of the front and back waist elastic members 54, 56 is provided by suitable supply sources 320. The web of waist elastic material 319 is also capable of stretching in at least the cross-machine direction.

The web of waist elastic material 319 is cut at a cutting station 323 to form a plurality of discrete pieces 322 of waist elastic material. The discrete pieces 322 are then bonded to the web side panel material 316 at a bonding station 325. In the illustrated embodiment, the discrete pieces 322 are oriented generally in the cross-machine direction before being bonded to the web of side panel material 316, which is traveling in the machine direction. The discrete pieces 322 of waist elastic material can be bonded to the side panel material 316 at the bonding station 325 using any suitable bonding technique. In one suitable embodiment, the discrete pieces of waist elastic material 322 are bonded to the web of side panel material 316 using pressure, adhesive, thermal and/or ultrasonic bonding.

With the discrete pieces of waist elastic material 322 bonded to the web of side panel material 316, the web of side panel material is cut in the machine direction by a slitter 326 aligned generally with the centerline of the web to form two continuous webs. The webs of side panel material 316 are then cut in the cross-machine direction a cutting station 327 to form a plurality of side panels 34, 35.

The side panels 34, 35 are then orientated with respect to and positioned in partially overlapping relationship with the bodyside liner material 104 using a suitable applicator device 328. In the cross-machine direction, each of the side panels 34, 35 extends laterally outward from the bodyside liner material 104 and overlaps the bodyside liner material by a suitable amount to permit bonding of the side panels to the bodyside liner.

As illustrated in FIG. 8, a continuous supply of material 140 used to form the outer cover 40 is provided from a suitable supply source 142. The central segments 54a, 56a of the front and back waist elastic members 54, 56 are attached to the outer cover material 40 as the outer cover material travels in the machine direction. More specifically, two continuous webs 143, 144 of waist elastic material are feed from suitable supply sources 145, 146. The waist elastic material webs 143, 144 are cut into segments 148, the segments are oriented in a cross-machine direction, and bonded to the outer cover material 140 at a cutting, orienting, and bonding station 147.

The outer cover material 140, which has central segments 54a, 56a of the front and back waist elastic members 54, 56 attached thereto, is transported over a laminator roll 150 and married with the bodyside liner material 104. The absorbent assemblies 114 are thereby sandwiched between the continuous bodyside liner and outer cover materials 104, 140. The inward portions of the of the side panels 34, 35 is also disposed between the bodyside liner material 104 and the outer cover material 140.

A bonding device 152, such as an ultrasonic bonder, is located downstream of the laminator roll 150 to bond the bodyside liner material 104, side panels 34, 35 and outer cover material 140 together. For example, these materials can be collectively transported between a rotary ultrasonic horn and an anvil roll adapted to point bond the bodyside liner material 104, side panels 34, 35 and outer cover material 140 together.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above without departing from the scope of the invention, it is intended that all matter contained in the above description and shown in the accompanying drawings shall be interpreted as illustrative and not in a limiting sense.

What is claimed is:

1. A method of manufacturing an absorbent article, the method comprising:
    moving a web of side panel material;
    moving waist elastic material separate from the web of side panel material;
    bonding the waist elastic material to the web of side panel material in direct face-to-face relationship;
    cutting the web of side panel material having the waist elastic material bonded directly thereto to form a side panel having a lateral waistband portion; and
    attaching the side panel having the lateral waistband portion to a chassis including a central waistband portion, the lateral waistband portion being generally aligned with the central waistband portion, the central waistband portion and the lateral waistband portion each having a top edge and a bottom edge defining a respective central waistband width and a lateral waistband width between the respective top edge and bottom edge, the central waistband width being substantially equal to the lateral waistband width.

2. The method as set forth in claim 1 further comprising stretching the waist elastic material prior to bonding the waist elastic material to the web of side panel material.

3. The method as set forth in claim 1 further comprising stretching the web of side panel material prior to bonding the waist elastic material to the web of side panel material.

4. The method as set forth in claim 1 further comprising stretching both the waist elastic material and the web of side panel material prior to bonding the waist elastic material to the web of side panel material.

5. The method as set forth in claim 1 wherein moving waist elastic material comprises moving a web of waist elastic material.

6. The method as set forth in claim 5 further comprising cutting the web of waist elastic material into discrete pieces of waist elastic material prior to bonding the waist elastic material to the web of side panel material.

7. The method as set forth in claim 1 wherein bonding the waist elastic material to the web of side panel material comprises at least one of thermal bonding, pressure bonding, adhesive bonding, and ultrasonic bonding.

8. The method as set forth in claim 1 wherein cutting the web of side panel material having the waist elastic material bonded thereto to form the side panel comprises a first cut of the web of side panel material in a direction of movement of the web of side panel material generally along a centerline of the web to form two continuous webs and then cutting each of the two continuous webs in a direction that is orthogonal to the first cut to form two side panels.

9. The method as set forth in claim 1 wherein bonding the waist elastic material to the web of side panel material comprises bonding the web of waist elastic material to the web of side panel material while both the web of waist elastic material and the web of side panel material are traveling in a direction of movement of the web of elastic waist material.

10. A method of manufacturing an absorbent article, the method comprising:
    moving a web of side panel material in a direction;
    moving a web of waist elastic material separate from the web of side panel material;
    cutting the web of waist elastic material into discrete pieces of waist elastic material;
    orienting the discrete pieces of waist elastic material in a direction that is generally orthogonal to the direction of movement of the web of side panel material;
    bonding the waist elastic material to the web of side panel material in direct face-to-face relationship;
    cutting the web of side panel material having the waist elastic material bonded directly thereto to form a side panel having a lateral waistband portion; and
    attaching the side panel having the lateral waistband portion to a chassis including a central waistband portion, the lateral waistband portion being generally aligned with the central waistband portion, the central waistband portion and the lateral waistband portion each having a top edge and a bottom edge defining a respective central waistband width and a lateral waistband width between the respective top edge and bottom edge, the central waistband width being substantially equal to the lateral waistband width.

11. A method of manufacturing an absorbent article, the method comprising:
    bonding a web of waist elastic material to a web of side panel material in direct face-to-face relationship;

cutting the web of side panel material having the web of waist elastic material bonded directly thereto to form at least two side panels, each side panel having a portion of the web of elastic material bonded thereto, each portion of the web of elastic material forming a lateral side segment including a lateral side segment width along a longitudinal axis of the lateral side segment;

bonding a central segment of waist elastic material to a chassis in at least one of a front waist region and a back waist region of the chassis, the central segment including a central segment width along a longitudinal axis of the central segment; and attaching the at least two side panels to the chassis such that the longitudinal axis of the lateral side segments of waist elastic material on the at least two side panels is generally aligned with the longitudinal axis of the central segment of waist elastic material in at least one of the front waist region and the back waist region of the chassis such that the lateral side segment width is substantially equal to the central segment width.

12. The method as set forth in claim 11 wherein cutting the web of side panel material having the lateral side segments of waist elastic material bonded thereto forms at least four side panels; wherein bonding the central side segment of waist elastic material to the chassis comprises bonding a central side segment of waist elastic material to each the front waist region and the back waist region of the chassis; and wherein attaching the at least two side panels to the chassis comprises attaching four side panels to the chassis with two of the side panels being attached to the front waist region and other two side panels being attached to the back waist region.

13. The method as set forth in claim 11 further comprising stretching the waist elastic material prior to bonding the waist elastic material to the web of side panel material.

14. The method as set forth in claim 13 further comprising stretching the web of side panel material prior to bonding the waist elastic material to the web of side panel material.

15. The method as set forth in claim 14 further comprising discontinuing the stretching of the side panel material to allow the web of side panel material having the lateral side segments of waist elastic material bonded thereto to exist in an un-stretched state after the web of side panel material having the lateral side segments of waist elastic material bonded thereto is cut to form at least two side panels and prior to attaching the at least two side panels to the chassis.

16. The method as set forth in claim 14 further comprises assembling a bodyside liner, an outer cover and an absorbent assembly disposed between the bodyside liner and the outer cover to form the chassis, wherein bonding the central segment of waist elastic material to the chassis comprises bonding the central segment of waist elastic material to an outer surface of the outer cover.

17. The method as set forth in claim 11, wherein the central segment of waist elastic material has an edge, further comprising generally aligning the edge of the central segment of waist elastic material with a waist edge of the at least one of the front waist region and the back waist region prior to bonding the central segment of waist elastic material to the chassis.

18. A method of manufacturing an absorbent article, the method comprising:
moving a web of side panel material,
moving a web of waist elastic material,
stretching a web of side panel material in a direction of movement of the web of side panel material;
stretching a web of waist elastic material in a direction of movement of the web of waist panel material;
bonding the web of waist elastic material to the web of side panel material in direct face-to-face relationship while both the web of waist elastic material and the web of side panel material are stretched;
cutting the web of side panel material having the web of waist elastic material bonded directly thereto to form at least two side panels, each side panel having a portion of the web of elastic material bonded thereto, each portion of the web of elastic material forming a lateral side segment including a lateral side segment width along a longitudinal axis of the lateral side segment, each side panel having a first edge opposite a second edge being connected by a waist opening edge and a leg opening edge;
bonding a central segment of waist elastic material to a chassis, the central segment including a central segment width along a longitudinal axis of the central segment; and
attaching the at least two side panels to the chassis such that the longitudinal axis of the lateral side segment of waist elastic material on each of the at least two side panels is generally aligned with the longitudinal axis of the central segment of waist elastic material on the chassis such that the lateral side segment width is substantially equal to the central segment width.

19. The method as set forth in claim 18 further comprising aligning an edge of the lateral side segment of waist elastic material that is orthogonal to the longitudinal axis with the first edge of each of the at least two side panels prior to bonding the web of waist elastic material to the web of side panel material.

20. The method as set forth in claim 18 further comprising aligning an edge of the lateral side segment of waist elastic material that is orthogonal to the longitudinal axis with the second edge of each of the at least two side panels prior to bonding the web of waist elastic material to the web of side panel material.

21. The method as set forth in claim 18 further comprising overlapping the central segment of waist elastic material bonded to the chassis with the lateral side segments of waist elastic material bonded to the at least two side panels prior to attaching the at least two side panels to the chassis.

22. The method as set forth in claim 18 wherein bonding the web of waist elastic material to the web of side panel material comprises one of thermal bonding the web of waist elastic material to the web of side panel material and ultrasonic bonding the web of waist elastic material to the web of side panel material.

23. The method as set forth in claim 18 wherein bonding the web of waist elastic material to the web of side panel material comprises point bonding the web of waist elastic material to the web of side panel material.

24. The method as set forth in claim 18 further comprising adding at least one of a visual cue and a tactile cue to each of the lateral side segments of waist elastic material bonded to the web of side panel material and adding at least one of a visual cue and a tactile cue to the central segment of waist elastic material bonded to the chassis.

* * * * *